(12) United States Patent
Schmidt et al.

(10) Patent No.: US 10,395,501 B2
(45) Date of Patent: Aug. 27, 2019

(54) MOBILE MONITORING DEVICE

(71) Applicant: MSA Europe GmbH, Jona (CH)

(72) Inventors: Ansgar Schmidt, Berlin (DE); Marcel Hahne, Hennigsdorf (DE); Gustavo Lopez, Sewickley, PA (US); Rene Klewer, Berlin (DE)

(73) Assignee: MSA Europe GmbH, Jona (CH)

( * ) Notice: Subject to any disclaimer, the term of this patent is extended or adjusted under 35 U.S.C. 154(b) by 0 days.

(21) Appl. No.: 15/123,323

(22) PCT Filed: Mar. 6, 2015

(86) PCT No.: PCT/EP2015/054751
§ 371 (c)(1),
(2) Date: Sep. 2, 2016

(87) PCT Pub. No.: WO2015/132393
PCT Pub. Date: Sep. 11, 2015

(65) Prior Publication Data
US 2017/0069193 A1    Mar. 9, 2017

(30) Foreign Application Priority Data

Mar. 6, 2014  (DE) .................. 10 2014 204 158

(51) Int. Cl.
*G08B 21/14* (2006.01)
*G08B 21/04* (2006.01)
(Continued)

(52) U.S. Cl.
CPC ....... *G08B 21/0453* (2013.01); *G08B 21/043* (2013.01); *G08B 21/0446* (2013.01);
(Continued)

(58) Field of Classification Search
None
See application file for complete search history.

(56) References Cited

U.S. PATENT DOCUMENTS 5,157,378 A    10/1992   Stumberg et al.
5,622,182 A    4/1997    Jaffe
(Continued)

FOREIGN PATENT DOCUMENTS

DE    102010027405 A1    1/2012
EP    2482264 A2         8/2012
(Continued)

*Primary Examiner* — John F Mortell
(74) *Attorney, Agent, or Firm* — The Webb Law Firm

(57) ABSTRACT

A mobile monitoring device, comprising a gas measurement device designed to read a value of a measured gas property of a gas and to provide a gas measurement signal dependent on the read value of the measured gas property; a body measurement device designed to read a value of a measured physical body property of a body of a person wearing the mobile monitoring device and to provide a body measurement signal dependent on the read value of the measured body property; and a control unit designed to receive the gas measurement signal and the body measurement signal and to control the mobile monitoring device dependent on a degree of correlation between a gas signal derived from the gas measurement signal and a body signal derived from the body measurement signal.

7 Claims, 3 Drawing Sheets

(51) Int. Cl.
*G08B 21/16* (2006.01)
*G06F 19/00* (2018.01)
*G08B 29/18* (2006.01)
*H04W 88/02* (2009.01)

(52) U.S. Cl.
CPC ......... *G08B 21/0492* (2013.01); *G08B 21/14* (2013.01); *G08B 21/16* (2013.01); *G06F 19/3418* (2013.01); *G08B 29/181* (2013.01); *H04W 88/02* (2013.01)

(56) References Cited

U.S. PATENT DOCUMENTS

| | | | |
|---|---|---|---|
| 6,072,396 A | 6/2000 | Gaukel | |
| 7,019,652 B2 | 3/2006 | Richardson | |
| 7,089,930 B2 | 8/2006 | Adams et al. | |
| 7,221,928 B2* | 5/2007 | Laird | A61B 5/04 455/404.1 |
| 8,400,317 B2* | 3/2013 | Johnson, Jr. | H04W 4/043 340/632 |
| 8,674,842 B2* | 3/2014 | Zishaan | F24F 11/30 340/627 |
| 9,311,805 B2* | 4/2016 | Zishaan | G08B 21/12 |
| 9,390,609 B2* | 7/2016 | Hogg | G08B 21/0453 |
| 9,754,472 B2* | 9/2017 | Johnson, Jr. | G06K 7/0095 |
| 9,877,650 B2* | 1/2018 | Muhsin | A61B 5/0002 |
| 2004/0017300 A1* | 1/2004 | Kotzin | G08B 21/0453 340/870.11 |
| 2007/0063850 A1 | 3/2007 | Devaul et al. | |
| 2007/0241261 A1* | 10/2007 | Wendt | G01D 9/005 250/221 |
| 2010/0081411 A1* | 4/2010 | Montenero | G08B 21/0233 455/404.2 |
| 2010/0217099 A1 | 8/2010 | LeBoeuf et al. | |
| 2011/0140913 A1* | 6/2011 | Montenero | G08B 21/0233 340/870.07 |
| 2012/0194334 A1* | 8/2012 | Worthington | G08B 21/043 340/521 |
| 2014/0081100 A1* | 3/2014 | Muhsin | A61B 5/0002 600/324 |

FOREIGN PATENT DOCUMENTS

| | | |
|---|---|---|
| WO | 2007033194 A2 | 3/2007 |
| WO | 2010108287 A1 | 9/2010 |
| WO | 2011094819 A1 | 8/2011 |

* cited by examiner

MOBILE MONITORING DEVICE

CROSS-REFERENCE TO RELATED APPLICATIONS

This application is the United States national phase of International Application No. PCT/EP2015/054751 filed Mar. 6, 2015, and claims priority to German Patent Application No. 10 2014 204 158.9 filed Mar. 6, 2014, the disclosures of which are hereby incorporated in their entirety by reference.

BACKGROUND OF THE INVENTION

Field of the Invention

The application relates to a mobile monitoring device, in particular to a mobile monitoring device that can be carried on the body of a task person such as a fireman, miner, policeman, etc., and which detects on the one hand a body condition of the task person such as a motion, a heartbeat rate, a breathing rate, etc. and on the other hand the condition of a gas that surrounds the mobile monitoring device. Furthermore, the application relates to a method for operating such a mobile monitoring device.

Description of the Related Art

A task person such as a miner, fireman or policeman usually wears a mobile monitoring device on himself that comprises a gas measurement device that reads a value of a measured gas property of a gas, the gas being in the environment around the mobile monitoring device, and provides a gas measurement signal dependent on the read value of the measured gas property. Therefore, the mobile monitoring device can determine, for example, whether the task person is exposed to a toxic gas and optionally trigger an acoustic alarm.

Furthermore, the conventional mobile monitoring device comprises a body measurement device that reads a value of a measured physical body property of the task person and provides a body measurement signal dependent on the read value of the measured body property. Therefore, the monitoring device can detect, for example, that the person has not moved anymore for a rather long time and emit an alarm in such a case.

The mobile monitoring device is usually carried not only during a certain use but during an entire workday by the task person.

The above-described mobile monitoring device furthermore comprises a control unit that receives the gas measurement signal and the body measurement signal, evaluates them and controls the monitoring device dependent on the evaluation.

Such a mobile monitoring device is known, for example from U.S. Pat. No. 5,157,378. The mobile monitoring device described in it is designed for a fireman and monitors the ambient temperature as well as the motion of the fireman. If a potentially dangerous situation is recognized, an alarm is activated. For example, the alarm is activated if the temperature exceeds a certain threshold value and/or if no motion was detected within a predetermined time span.

U.S. Pat. No. 7,089,930 B2 discloses a mobile monitoring device that is designed to automatically go into an energy-saving mode dependent on measured properties.

SUMMARY OF THE INVENTION

In summary, one embodiment provides a mobile monitoring device (1) comprising a gas measurement device (11) that is designed to read a value of a measured gas property of a gas, the gas being in the environment around the mobile monitoring device (1), and to provide a gas measurement signal (1111) dependent on the read value of the measured gas property; a body measurement device (12) that is designed to read a value of a measured physical body property of a body of a person wearing the mobile monitoring device (1) and to provide a body measurement signal (1211) dependent on the read value of the measured body property; and a control unit (13) that is designed to receive the gas measurement signal (1111) and the body measurement signal (1211) and to control the mobile monitoring device (1); characterized in that the control unit (13) comprises a correlator (133) that is designed to determine a correlation signal (1331) dependent on a degree of correlation between a gas signal (1311) derived from the gas measurement signal (1111) and a body signal (1321) derived from the body measurement signal (1211), wherein the control unit (13) is designed to control the mobile monitoring device (1) dependent on the correlation signal (1331).

Another embodiment provides a mobile monitoring device, comprising: a first measuring device that detects a gas in the environment surrounding the monitoring device and generates a gas signal based on the detected gas; a second measuring device that detects a physical trait associated with a user of the mobile monitoring device and generates a body signal based on the detected physical trait; a correlator that generates a correlation signal utilizing both of the gas signal and the body signal; and a control unit that controls the mobile monitoring device dependent on the correlation signal.

A further embodiment provides a method, comprising: detecting, using a gas measurement device of a mobile monitoring device, a gas in the environment surrounding the monitoring device; generating, using the gas measurement device, at least one gas signal based on the detecting of the gas; detecting, using a body measurement device of the mobile monitoring device, a physical trait associated with a user of the mobile monitoring device; generating, using the body measurement device, at least one body signal based on the detecting of the physical trait; generating, using a correlator of the mobile monitoring device, a correlation signal utilizing the body signal and the gas signal; and controlling, using the control unit of the mobile monitoring device, the mobile monitoring device dependent on the correlation signal.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DESCRIPTION OF THE INVENTION

Figure 1:
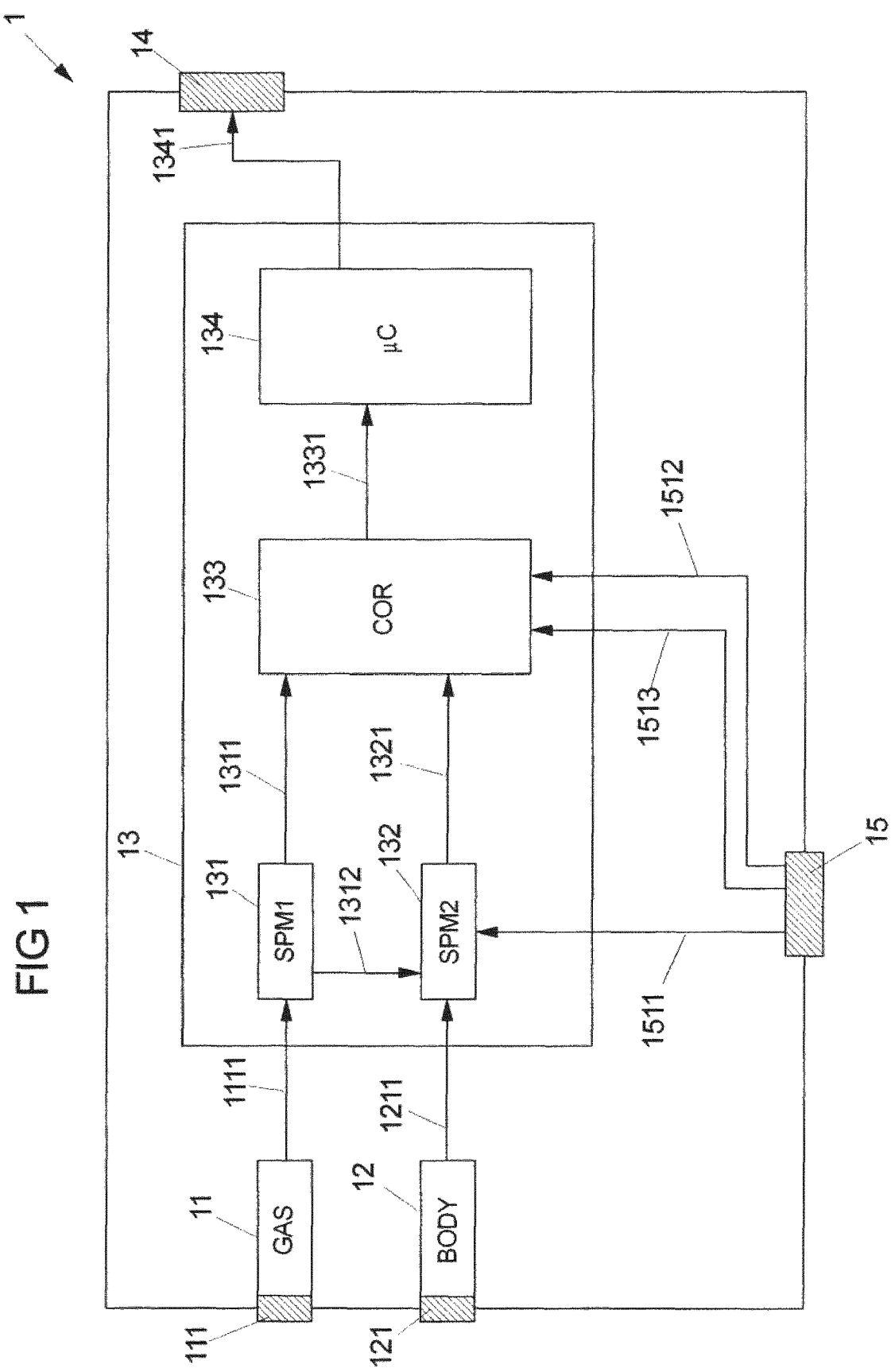
FIG. 1 is a schematic and exemplary view of an embodiment of a mobile monitoring device according to the principles of the present invention.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout the specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of various embodiments. One skilled in the relevant art will recognize, however, that the various embodiments can be practiced without one or more specific details, or with other methods, components, materials, etc. In other instances, well known structures, materials, or operations are not shown or describe in detail to avoid obfuscation.

The previously known mobile monitoring devices have the disadvantage that in them measured properties that are different from each other are always considered independently of each other. As a result, it can occur that false alarms are generated and/or that no alarms are generated although the person wearing the mobile monitoring device is in a dangerous situation.

It would be useful to have a mobile monitoring device and a method for operating a mobile monitoring device in which an alarm can be generated in a reliable manner in certain specific situations.

The monitoring device of the present invention is particularly suited for detecting a dangerous situation in which a task person, who is wearing the mobile monitoring device, is situated.

The mobile monitoring device can be designed as an independent device or—completely or partially—as part of an already existing piece of equipment such as, for example, a helmet, a radio or a breathing mask or the like. The components of the mobile monitoring device, in particular the gas measurement device, the body measurement device and the control unit as well as their subunits, therefore do not necessarily have to be installed in a housing but can also be distributed in or on one or more already present equipment pieces of the person.

The mobile monitoring device in accordance with an embodiment comprises a gas measurement device that is designed to read a value of a measured gas property of a gas surrounding the mobile monitoring device. Furthermore, the gas measurement device is designed to provide a gas measuring signal dependent on the read value of the measured gas property. The measured gas property can be, for example, the toxicity of the gas, the explosiveness of the gas, the gas pressure, the gas temperature and/or an oxygen content of the gas. In particular, the gas measurement device can also read several values of measured gas property that differ from each other. The gas measurement device provides a gas measuring signal dependent on the read value or of the read values.

The mobile measuring device in accordance with an embodiment furthermore comprises the body measurement device that is designed to read the value of a measured physical body property (also designated in the following simply as "measured body property") of a body of a person wearing the mobile monitoring device. The person wearing the monitoring device can be, for example, a task person such as a fireman, a police man or a miner. The body measurement device provides a body measurement signal in dependence on the read value of the measured body property. An embodiment is basically not limited to a certain measured body property. The measured body property can be, for example, a motion property such as an acceleration and/or a speed and/or a position. To this end the body measurement device comprises, for example, an acceleration sensor that detects a one-dimensional or multi-dimensional motion of the body of the person wearing the mobile monitoring device. However, the measured physical body property can also be a measured property that is indicative for the functionality of the heart and/or of the lung or of some other organ of the body of the person and/or a measured property indicative of a body temperature of the person. The body measurement device of the mobile monitoring device can also read values of several measured physical body properties of the body and generate and provide the body measurement signal dependent on the read values of the measured body properties.

Furthermore, the mobile monitoring device comprises the control unit, which is designed for receiving the gas measurement signal and the body measurement signal and for controlling the mobile monitoring device. In particular, the control unit is designed to control the mobile monitoring device depending on the gas measurement signal and on the body measurement signal, for example, in that the control unit generates an alarm dependent on these two signals and/or puts the mobile monitoring device in an energy-saving mode.

For these purposes the control unit of the mobile monitoring device comprises a correlator that is designed to determine a correlation signal dependent on a degree of correlation between a gas signal derived from the gas measurement signal and a body signal derived from the body measurement signal. In particular, the control unit is designed to control the mobile monitoring device dependent on the correlation signal, that is, dependent on a correlation between the gas signal and the body signal. The control unit preferably considers these two signals not in isolation from one another but rather in their commonality in order to adjust a single control factor, e.g., to generate an alarm signal.

For example, a first signal evaluation means or mechanism is provided that evaluates the gas measurement signal and provides the gas signal dependent on the evaluation. Furthermore, by way of example a second signal evaluation means or mechanism is provided that evaluates the body measurement signal and provides the body signal dependent on the evaluation. The correlator determines a degree of correlation between these two signals, for example, by comparing the body signal with the gas signal. In dependence on the correlation signal being indicative therefor, the control unit controls the mobile monitoring device. For these purposes the control unit includes, e.g., a controller that receives the correlation signal and adjusts a control factor of the mobile monitoring device dependent on the correlation signal. The adjusting of the control factor by the controller effects, for example, the generation and the optional emission of an alarm signal by the mobile monitoring device and/or the putting of the mobile monitoring device in an energy-saving mode.

The advantage of the correlator provided in accordance with the embodiment resides in particular in the fact that the gas measurement signal and the body measurement signal are not considered separately from one another but rather at the same time and that a decision can be made by the simultaneous consideration of the gas signal and of the body signal by the controller whether the mobile monitoring device must generate an alarm or not. Thus, it is possible for example that an alarm is generated upon a body signal that deviates only slightly from a norm because, for example, at the same time the gas signal also deviates from a norm, for example, indicating the presence of a high toxicity or explosiveness. On the other hand, it can be possible that the body signal deviates more distinctly from a norm but the gas signal is indicative for a normal gas environment. Accordingly, this instance would not result in the generation of an alarm signal.

If the body signal indicates, for example, a rather long time of the body at a standstill, the control unit does not effect the shift into an energy-saving mode if at the same time the gas signal indicates an irregularity in the gas environment. Therefore, it can be avoided that the monitoring device shifts into an energy-saving mode and consequently does not detect a dangerous situation conditioned by the gas environment.

Such correlations between the gas signal on the one hand and the body signal on the other hand are determined by the correlator of the control unit. The correlator also ensures that the control unit adjusts a control factor dependent on the gas signal as well as of the body signal and not, for example, only dependent on the gas signal or of the body signal. Rather, the correlator allows the control unit to observe the gas signal as well as the body signal simultaneously in order to adjust a same control factor of the mobile monitoring device such as, for example, the alarm signal or the energy-saving mode signal. The correlations described above by way of example between the gas signal on the one hand and the body signal on the other hand are detected by the degree of correlation and communicated by means of the correlation signal.

For example, the correlator generates the correlation signal dependent on a correlation in time between the gas signal and the body measurement signal. The degree of correlation, for example, is indicative of a correlation in time between the gas signal and the body signal and determined, for example, by an interval of time between the occurrence of a deviation of the gas signal from a gas signal threshold value and the occurrence of a deviation of the body signal from a body signal threshold.

The longer this time interval is, the lower the degree of correlation. The shorter the time interval is, the greater the degree of correlation. Therefore, for example, if both deviations occur approximately simultaneously or shortly after one another then the degree of correlation is high and the control unit generates, for example, the alarm signal. If both deviations occur with a comparatively great delay, then the degree of correlation is low and the control unit, for example, does not generate the alarm signal. Both deviations can in particular also be slight; if the gas signal and/or the body measurement signal deviate significantly from the particular threshold value, this information alone is sufficient for generating the alarm signal. The slighter the deviation is, the more significant in particular the correlation in time between the slight deviations of the gas signal and of the body signal from the particular threshold values is: If the degree of correlation is high and if deviations are present, even if only slight, then this information can be sufficient for generating the alarm signal.

Another advantage of the correlator is that using the simultaneous consideration of the gas signal and of the body signal, more information about the actual surroundings of the person and about the person can be determined than from only the sum of the information from the gas signal on the one hand and from the body signal on the other hand, which will be explained using an example.

For example, the gas measurement device is only designed to read values of measured gas properties of certain gases. The gas signal obtained by means of the gas measurement device can therefore, for example, be indicative of the presence of a first gas and of a second gas. If the body signal indicates at the same time or at a slight interval of time from such a gas signal that an abnormal body state prevails, for example, "dragging locomotion", then the correlator can conclude based on the simultaneous consideration of both signals, for example, that a third gas is also present because the third gas, for example, is then frequently present when the first and the second gases are also present and results in weaknesses of the body, that is, for example, in a dragging locomotion of the person. It shall be explained using this example that the correlation between the gas signal on the one hand and the body signal on the other hand cannot only be a characteristic of time but also of content.

Accordingly, the correlator is preferably designed to determine the correlation signal dependent on a correlation in time and/or dependent on a correlation of content between the gas signal and the body signal. For example, the correlation in time and/or the correlation of content define the degree of correlation.

For example, the mobile monitoring device furthermore comprises a radio signal measuring device designed to read a value of a strength of an external radio signal and to provide a radio measurement signal dependent on the read value of the strength of the external radio signal. The correlator is preferably designed to determine the correlation signal also dependent on the radio measurement signal, for example, dependent on a degree of correlation between the radio measurement signal on the one hand and the gas signal and/or the body signal on the other hand. This variant has the advantage that in order to control the mobile monitoring device, for example, for generating an alarm signal, in addition to the gas signal and the body signal, the strength of the external radio signal is additionally considered. The strength can be indicative, for example, of a position of the person, for example, of an absolute position inside a wireless network in which the monitoring device is active, and/or of a position relative to another task person and/or of a position relative to an object or to a building in an area of use. The external radio signal is provided, for example, by a base station that forms the wireless network and/or by a piece of equipment of an adjacent task person.

Other exemplary embodiments of the mobile monitoring device are described in the following. The additional features of these exemplary embodiments can be combined with each other in various ways for forming other embodiments as well as with the various features already described above in as far as they were not expressly described as being alternative to each other.

In a preferred embodiment of the mobile monitoring device the correlator includes a comparison unit that is designed to receive the gas signal and the body signal and to carry out the following three comparisons: a comparison between the gas signal and a predetermined gas signal threshold value, a comparison between the body signal and a predetermined body signal threshold value, and a comparison between the gas signal and the body signal. The comparison unit of the correlator generates the correlation signal dependent on the comparison results. Therein, the comparison between the gas signal and the body signal determines the degree of correlation, for example the correlation in time, between the gas signal on the one hand and the body signal and the other hand. Therefore, the degree of correlation is determined, for example, by the comparison of the gas signal with the body signal.

If the correlation signal indicates, for example, that the gas signal has exceeded or dropped below a predetermined gas signal threshold value, the control unit can effect the generation of an alarm signal. For example, the alarm signal is generated if the gas signal is indicative of a toxicity value that is higher than an admissible value. The same applies in a logical manner for the body signal. If the correlation signal indicates that the body signal has exceeded or dropped below the predetermined body signal threshold value, the body signal is therefore indicative of, for example, a cardiac insufficiency, a pulmonary insufficiency and/or for a too high body temperature or some other critical state of the body of the person wearing the monitoring device, the control unit can then effect the generation of a corresponding alarm signal. Furthermore, however, not only the body signal and the gas signal are compared with a corresponding threshold value but in particular the body signal and the gas signal are also compared with one another, for example, with regard to the time, so that the generation of an alarm signal can also be effected if neither the gas signal nor the body signal exceeds or drops below the corresponding threshold value but the gas signal and the body signal indicate in their commonality that the person wearing the monitoring device is in a dangerous situation. If the gas signal as well as the body signal are in the vicinity of a predetermined threshold value within a predetermined time period it can be absolutely appropriate to generate an alarm signal because the situation in which the person is present is absolutely to be estimated as dangerous. Furthermore, it can be prevented that the mobile monitoring device is put in an energy-saving mode if the body signal is indicative of a state of rest for a rather long time but the gas signal indicates irregularities in the condition of the surrounding gas.

In another embodiment of the mobile monitoring device the first signal evaluation mechanism comprises an analysis unit designed to carry out the evaluation of the gas measurement signal and to generate the gas signal and in addition to generate a control signal dependent on the evaluation. The second signal evaluation mechanism preferably comprises a weighting unit to which this control signal is supplied, wherein the weighting unit is designed to weigh the body measurement signal dependent on the control signal and to provide a weighted body measurement signal.

This embodiment has the advantage that the sensitivity of the mobile monitoring device can be adapted dependent on the current condition of the instantaneous surrounding of gas. For example, if the analysis unit determines that the gas measurement signal does not indicate a critical gas situation, that the gas therefore has a condition that is not dangerous for the person wearing the mobile monitoring device, then the control signal effects a rather low weighting of the body measurement signal, for example, a multiplication of the body measurement signal by a value of approximately 1 or less than 1 such as, for example, 0.5 or 0.1. This has the result that the body signal that is generated dependent on the weighted body measurement signal does not result so rapidly in an exceeding or dropping below the predetermined body signal threshold value and therefore also does not lead to a premature generation of an alarm signal.

On the other hand, if the analysis unit determines that the gas measurement signal is indeed indicative of a dangerous situation, for example, because the gas measurement signal indicates that the toxicity of the gas is higher than usual, the air pressure is especially low or especially high, the temperature especially high or the like, the control signal effects in the weighting unit a stronger weighting of the body measurement signal, for example, a multiplication of the body measurement signal by a value greater than 1 so that even less pronounced irregularities in the body measurement signal can have the result of generating an alarm signal.

In another embodiment of the mobile monitoring device the second signal evaluation mechanism comprises a feature extractor, a storage device and a comparator. The feature extractor is designed to extract features from the body measurement signal or from the weighted body measurement signal (in as far as this weighting unit is provided) and to provide a feature signal. The storage device is designed to store a number of measured body property profiles. Finally, the comparator is designed to compare the feature signal with a measured body property profile stored in the storage device and to generate and provide the body signal dependent on the comparison.

These three components of the second signal evaluation mechanism facilitate the generating of the body signal. It is provided at first that the feature extractor extracts certain features from the body measurement signal. Such a feature extraction is basically known from the prior art. A number of measured body property profiles are stored in the storage device. The measured body property profiles are, for example, motion profiles of which a first one can be indicative of a "normal" course of motion and a second one can be indicative of a first "abnormal" course of motion and a third one for a second "abnormal" course of motion, etc. The same logically applies to other measured body properties, for example, for a heartbeat rate, for a breathing rate, for a body temperature and/or a blood pressure, etc. The comparator compares the feature signal with the stored measured body property profiles. The body signal provided by the comparator can be indicative, for example, of a certain measured body property profile that largely fitted the feature signal. For example, the body signal may indicate that the motion, the heartbeat rate, the body temperature, the breathing rate and/or a blood pressure are "normal," slightly deviate from the norm, greatly deviate from a norm, etc. Then the correlator compares this body signal with the gas signal and provides the correlation signal dependent on the comparison, that is, dependent on the degree of correlation between these signals. Based on this correlation signal, the control unit decides whether an alarm signal is to be generated and/or whether the mobile monitoring device is to be put into an energy-saving mode.

In another embodiment of the mobile monitoring device, the storage device is designed for receiving the measured body property signal. Furthermore, the storage device includes a data logger designed for the continuous recording of data being indicative of the measured body property signal received during a past time period of a predetermined duration. This has the advantage that the comparator receives a feature signal that is indicative of a current value of the measured body property and compares it with a measured body property profile that is indicative of values of the measured body property that were recorded in the past. In this manner deviations can be more readily detected and irregularities in the measured body property recognized. For example, the data logger records the history of the speed and of the direction of motion of the person, which facilitates the recognizing of abnormal motion states such as a "dragging locomotion" or a "staggering."

Furthermore, the storage device preferably comprises a profile generation unit designed to generate measured body property profiles dependent on the data recorded by the data logger. Therefore, the mobile monitoring device can automatically prepare measured body property profiles and file them in the storage device. Such measured body property profiles, that is, data being indicative of values of measured body properties recorded in the past, can be compared by the comparator with current values of measured body properties (expressed by the feature signal). In this manner deviations from previous values and therefore suspicious items that can indicate a dangerous situation can be more readily detected.

In another embodiment the profile generation unit is furthermore designed to file the measured body property profiles dependent on a user recognition entered by means of an input means or unit into the mobile monitoring device. The mobile monitoring device therefore preferably comprises said input unit via which the person wearing the mobile monitoring device can input a user recognition. In this manner specific measured body property profiles can be generated for the particular user and filed in storage areas of the storage device provided for this.

In another embodiment the mobile monitoring device furthermore comprises a transmitter designed to transmit the alarm signal to a monitoring center via a wireless network. The mobile monitoring device is therefore, for example, a mobile terminal operating in a wireless network as a client. When an alarm signal is generated, the transmitter of the mobile monitoring device sends this alarm signal to the monitoring center. The alarm signal can indicate, for example, an identity of the person who is wearing the monitoring device and/or indicate the current location of the mobile monitoring device. For these purposes the mobile monitoring device comprises, for example, a GPS receiver or some other localization module designed to determine the current location of the mobile monitoring device. Such location data can be integrated into the alarm signal before it is transmitted from the transmitter to the monitoring center.

In addition or alternative to the emission of the alarm signal the control unit is designed according to other embodiments to output the alarm signal in the form of an optical signal and/or in the form of an acoustic signal, e.g., by means of LEDs, a loudspeaker or the like.

Methods in accordance with the present invention can be implemented to appropriately correspond to the above-described embodiments of the mobile monitoring device, in particular as they are defined in the claims.

The description now provides a detailed explanation using the exemplary embodiments presented in the figures.

FIG. 1 shows a schematic and exemplary view of an embodiment of a mobile monitoring device 1 in accordance with an embodiment of the invention. In this view only certain components are shown but not components that are to be found customarily on or in the mobile monitoring device 1 such as, for example, a battery, a display, an output device, etc.

The mobile monitoring device 1 is suited for monitoring the personal situation of a task person such as, for example, a miner, a fireman or a policeman, etc. The battery-operated mobile monitoring device 1 is carried by such a task person during a use, for example, during underground work. The mobile monitoring device 1 can be implemented to this end as an independent device with a separate housing or as part of an already existing piece of equipment, for example, as part of a breathing mask, of a radio device, of a helmet, etc.

The mobile monitoring device 1 is suited on the one hand for analyzing the condition of the gas surrounding the mobile monitoring device 1 and on the other hand for monitoring a measured physical body property whose value is indicative of a physical state of the task person. For these purposes the mobile monitoring device comprises on the one hand a gas measurement device (GAS) 11 and on the other hand a body measurement device (BODY) 12. These devices read values of at least one measured gas property and values of at least one measured body property by means of a gas measurement interface 111 and by means of a body measurement interface 121. The measured gas property can be, for example, a toxicity of the gas, an explosiveness of the gas, an oxygen content of the gas, a temperature and/or a pressure of the gas.

The measured body property is indicative of a body parameter, for example, of a body motion such as a body speed, indicative of a heartbeat rate, of a breathing rate, of a body temperature and/or of a blood pressure.

The configuration of the gas measurement device 11 and of the body measurement device 12 goes according to the selected measured body property and according to the selected measured gas property. For example, if the measured body property is a body motion property, the body measurement device 12 comprises, for example, one or more acceleration sensors for detecting a one-dimensional or multi-dimensional motion of the body or of a body part of the person wearing the mobile monitoring device 1. In order to detect a heartbeat rate and/or a breathing rate a plurality of possibilities are known from the prior art and the body measurement device 12 would in this case be correspondingly designed. The same applies to the detection of a body temperature.

The gas measurement device 11 provides a gas measurement signal 1111 and the body measurement device 12 provides a body measurement signal 1211. These two signals 1111 and 1211 are supplied to a control unit 13 of the mobile monitoring device 1.

The control unit 13 controls the mobile monitoring device 1 in particular dependent on these two signals 1111 and 1211. On the one hand the control unit 13 compares a gas signal 1311 derived from the gas measurement signal 1111 with the gas signal threshold value 1512, a body signal 1321 derived from the body measurement signal 1211 with a body signal threshold value 1513 and also compares in particular the gas signal 1311 with the body signal 1321 in particular as regards the time. The control unit 13 detects dependent on these three comparisons whether the person wearing the mobile monitoring device 1 is in a dangerous situation or not.

A dangerous situation can result, for example, by the fact that the toxicity of the gas being in the environment around the mobile monitoring device 1 has significantly exceeded the predetermined gas signal threshold value 1512. A dangerous situation can also result due to the fact that the body signal 1321 being indicative of a rather long standstill of motion, a cardiac insufficiency, a too high body temperature and/or a pulmonary insufficiency, that is, the body signal 1321 deviates significantly from the predetermined body signal threshold value 1513.

However, a dangerous situation can also arise when neither the gas signal 1311 nor the body signal 1321 significantly exceed or drop below the predetermined threshold values 1512, 1513 but indicate in their commonality that the situation of the task person is to be classed as dangerous and accordingly an alarm signal 1341 is to be produced.

The control unit 13 provides the alarm signal 1341, for example, to a transmitter 14 of the mobile monitoring device 1, wherein the transmitter 14 transmits the received alarm signal 1341, for example, to a monitoring center. Therefore, the mobile monitoring device 1 is, for example, a client in a wireless network. The alarm signal 1341 can furthermore be enriched with more data, for example, with data being indicative of the current location of the mobile monitoring device 1 and/or being indicative of a recognition of the task person wearing the mobile monitoring device 1. For these purposes the mobile monitoring device 1 may include, for example, a GPS receiver (not shown in FIG. 1).

However, the control unit 13 uses the gas signal 1311 and the body signal 1321 not only for producing the alarm signal 1341 but, for example, also in order to determine whether the mobile monitoring device 1 is to be put into an energy-saving mode. Also for these purposes, the control unit 13 does not consider the gas signal 1311 and the body signal 1321 in isolation from one another but rather simultaneously. If, for example, the body signal 1321 indicates that the mobile monitoring device 1 has not been used for a rather long time, that is, was not moved, then the control unit 1 effects the transfer into an energy-saving mode only if also the gas signal 1311 is not indicative of a dangerous situation.

The above examples illustrated that it is important not to consider the gas signal 1311 and the body measurement signal 1321 in isolation from one another but rather to correlate both signals with one another in addition to customary threshold value comparisons. Therefore, the control unit 13 determines a degree of correlation, in particular a degree of correlation in time, between the gas signal 1311 on the one hand and the body signal 1321 on the other hand, for example, by means of this comparison. In this manner the generation of false alarms can be minimized and it can furthermore be avoided that the alarm signal 1341 is not produced even though the task person wearing the mobile monitoring device 1 is momentarily present in a situation to be classified as dangerous. For these purposes the control device 13 of the mobile monitoring device 1 comprises a first signal evaluation unit (SPM 1) 131 for evaluating the gas measurement signal 1111 and for providing the gas signal 1311, and comprises a second signal evaluation unit (SPM2) 132 for evaluating the body measurement signal 1211 and for providing the body signal 1321.

In addition, the control device 13 comprises a correlator (COR) 133 that receives and evaluates the gas signal 1311 and the body signal 1321 and provides a correlation signal 1331 dependent on the evaluation. The correlation signal 1331 is supplied to a controller (µC) 134 that controls the mobile monitoring device 1 dependent on the correlation signal 1331, and therefore, for example, effects the production and emission of the alarm signal 1341 by means of the transmitter 14 and/or the putting of the mobile monitoring device 1 in an energy-saving mode or in a normal operating mode.

Moreover, the mobile monitoring device 1 comprises an input device 15 via which a user recognition 1511, the gas signal threshold value 1512 and the body signal threshold value 1513 can be inputted. The input device 15 can basically be designed in any manner; it can be, for example, a customary programming interface and/or input keys that can be operated by a user of the mobile monitoring device 1.

The just-designated components of the control unit 13 of the mobile monitoring device 1 are described in detail in the following with reference made to FIG. 2 to FIG. 4.

Figure 2:
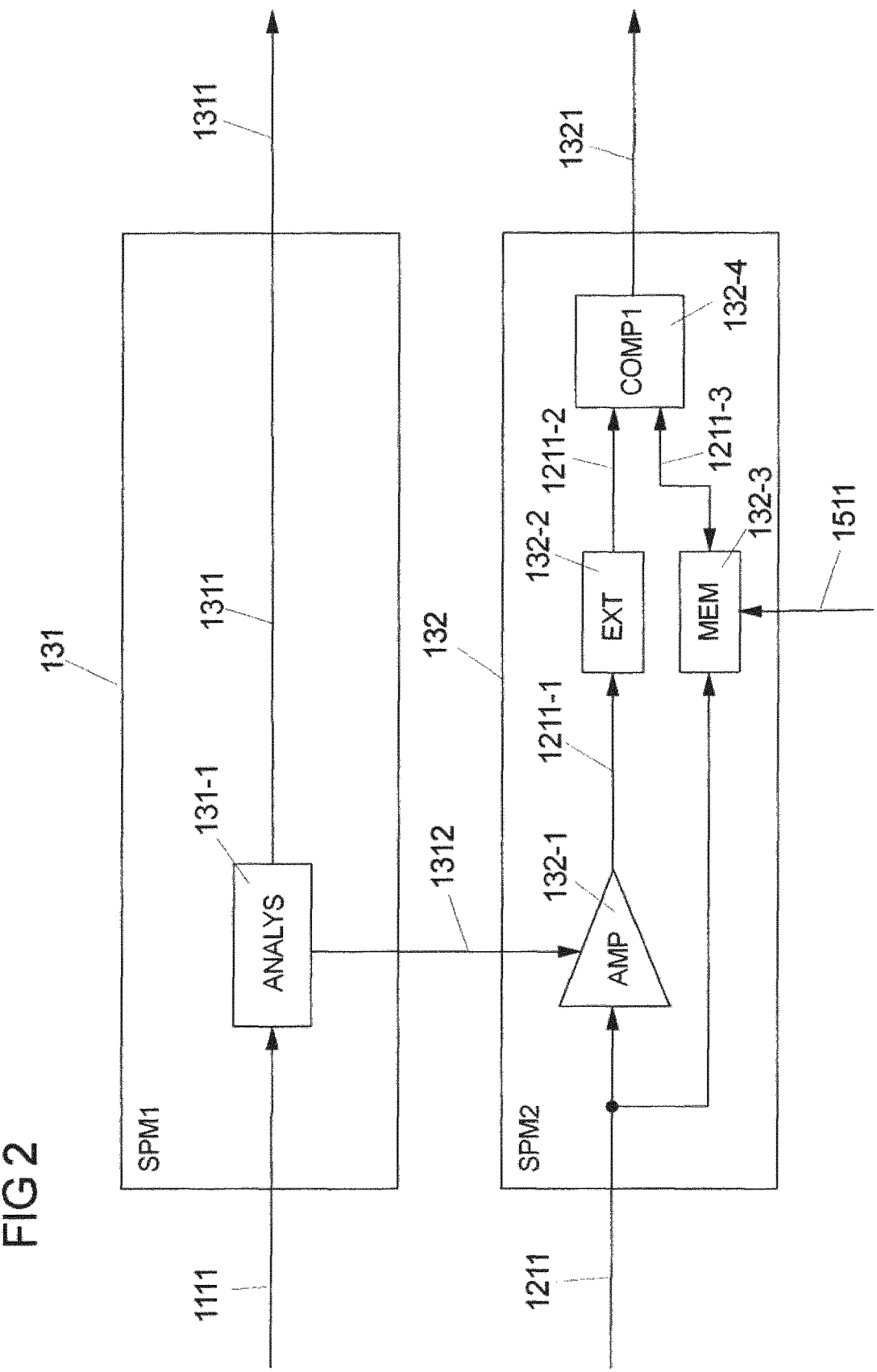
FIG. 2 are schematic and exemplary views of embodiments of signal evaluation means of the mobile monitoring device according to the principles of the present invention.

At first, FIG. 2 shows schematic and exemplary views of embodiments of the first signal evaluation unit 131 and of the second signal evaluation unit 132.

The first signal evaluation unit 131 converts the gas measurement signal 1111 into the gas signal 1311. For this purpose the first signal evaluation unit 131 comprises an analysis unit (ANALYS) 131-1. The analysis unit 131-1 evaluates, for example, the gas measurement signal 1111 provided by a gas sensor provided, for example, in the gas measurement device 11 and provides the gas signal 1311 dependent on the evaluation. The analysis unit can be a simple filter unit or, however, a more complex evaluation unit depending of the configuration of the gas measurement device 11. In dependence on the evaluation, the analysis unit 131-1 not only provides the gas signal 1311 but also provides a control signal 1312 that is supplied to the second signal evaluation unit 132.

The second signal evaluation unit 132 receives the body measurement signal 1211 and provides the body signal 1321 dependent on the signal evaluation. In the exemplary embodiment shown in FIG. 2 the second signal evaluation unit 132 comprises a weighting unit (AMP) 132-1 to which the control signal 1312 of the analysis unit 131-1 is supplied. The weighting unit 132-1 is an optional unit of the signal evaluation unit 132. The mobile monitoring device 1 can basically also be implemented without this weighting unit 132-1. However, the weighting unit 132-1 has the advantage that the sensitivity regarding the detection of the condition of the body can be adapted dependent on the current condition of the gas surrounding the mobile monitoring device. If the analysis unit 131-1 determines using the gas measurement signal 1111, for example, that the toxicity of the gas is indeed to be classified as significant, it produces a control signal 1312 in such a manner that it has the result in the weighting unit 132-1 that the body measurement signal 1211 is amplified. Anomalies in the body measurement signal 1211 therefore tend to result in an alarm signal 1341 because it more rapidly exceeds said threshold value. On the other hand, the body measurement signal 1211 can also be attenuated by the weighting unit 132-1, for example, if the analysis unit 131-1 determines using the gas measurement signal 1111 that the current condition of the gas is to be classified as a good or compatible and anomalies in the body measurement signal should not directly result in the generation of an emission of the alarm signal 1341.

Nevertheless, the weighting unit 132-1 provides a weighted body measurement signal 1211-1 dependent on the control signal 1312 and dependent on the body measurement signal 1211. The weighted body measurement signal 1211-1 is supplied to a feature extractor (EXT) 132-2. The feature extractor 132-2 extracts features from the weighted body measurement signal 1211-1 (and from the body measurement signal 1211 if no weighting unit 132-1 is installed) and provides a corresponding feature signal 1211-2. The method of operation of such a feature extractor is basically known from the prior art.

Furthermore, the second signal evaluation means 132 comprises a storage device (MEM) 132-3. The storage device 132-3 stores a number of measured body property profiles, what will be explained in more detail later with reference made to FIG. 3. The feature extractor 132-2 and the storage device 132-3 are followed by a comparator (COMP1) 132-4. The comparator 132-4 compares the feature signal 1211-2 with measured body property profiles in the storage device 132-3. Therefore, the comparator 132-4 accesses the storage device 132-3 or, however, the storage device 132-3 provides the measured body property profiles to the comparator 132-4 in the form of corresponding signals 1211-3 so that the comparator 132-4 can carry out said comparison.

The comparison carried out by the comparator 132-4 serves to determine whether the values of the detected measured body property coincide with a certain profile or deviate with a certain difference from a certain profile. For example, if the measured body property is a motion property, a first motion profile is indicative, for example, of a normal movement of the task person, a second motion profile is indicative of a normal state of rest of the task person and a third motion profile is indicative of an "abnormal" state of rest of the task person, etc. The comparator 132-4 provides the body signal 1321 dependent on the comparison. Therefore, the body signal 1321 indicates whether, for example, the motion, the heartbeat rate, the breathing rate or the like agree with a certain profile or deviates with a certain deviation from a certain profile. This body signal 1321 is supplied in addition to the gas signal 1311 to the correlator 133.

Figure 4:
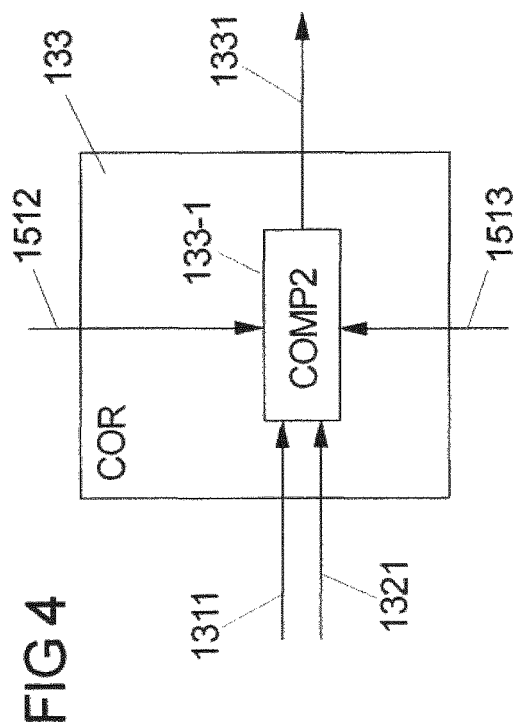
FIG. 4 is a schematic and exemplary view of an embodiment of a correlator of the mobile monitoring device according to the principles of the present invention.

FIG. 4 schematically shows an embodiment of the correlator 133. The correlator 133 carries out the above-described three comparisons and comprises for this purpose a comparison unit (COMP2) 133-1. On the one hand the comparison unit 133-1 compares the gas signal 1311 with the predetermined gas signal threshold value 1512 and on the other hand the comparison unit 133-1 compares the body signal 1321 with a predetermined body signal threshold value 1513. The comparison takes place in order whether a value of the gas signal 1311 or of the body signal 1321 exceeds or drops below a threshold value. The comparison unit 133-1 can also compare the gas signal 1311 or the body signal 1321 with a plurality of threshold values.

However, in addition to these two comparisons the comparison unit 133-1 also makes a comparison between the gas signal 1311 on the one hand and the body signal 1321 on the other hand. To this extent the comparison unit 133-1 determines a type of correlation, in particular a correlation in time between these two signals 1311 and 1321. The comparison unit 133-1 provides the correlation signal 1331 dependent on the three comparisons. This signal 1331 is supplied to the controller 134 that decides based on it whether the alarm signal 1341 is to be emitted and/or whether the mobile monitoring device 1 is to be put into an energy-saving mode or into a normal operating mode. It is important that this decision by the controller 134 does not take place by a separate and isolated consideration of the gas signal 1311 on the one hand and of the body signal 1321 on the other hand but rather that a simultaneous consideration of the gas signal 1311 and also of the body signal 1321 takes place by means of the correlator 133 in order to adjust a single control factor such as, for example, the alarm signal and/or the control factor, that has the result that the mobile monitoring device 1 is put into alarm or in the energy-saving mode.

For example, the correlator 133 generates the correlation signal 1331 dependent on a correlation in time between the gas signal 1311 and the body measurement signal 1321. The degree of correlation is indicative, for example, of a correlation in time between the gas signal 1311 and the body signal 1321 as determined, for example, by an interval of time between the occurrence of a deviation of the gas signal 1311 from the gas signal threshold value 1512 and the occurrence of a deviation of the body signal 1321 from a body signal threshold value 1513. The longer this time interval is, the lower the degree of correlation. The shorter the time interval is, the greater the degree of correlation. Therefore, if both deviations occur, for example, approximately at the same time or shortly after one another, then the degree of correlation is high and the control unit 13 generates, for example, the alarm signal 1341. If both deviations occur with a comparatively large delay, then the degree of correlation is low and the control unit 13 does not, for example, generate the alarm signal 1341.

In particular, both deviations can also turn out to be slight; if the gas signal 1311 and/or the body measurement signal 1321 differs significantly from the respective threshold value 1512, 1513, then this information alone is sufficient for generating the alarm signal 1341. The lesser the deviation turns out to be, the more significant in particular the correlation in time is between the slight deviations of the gas signal 1311 and of the body signal 1321 from the respective threshold values 1512, 1513: If the degree of correlation is high and deviations are present, even if only slight ones, this information can be sufficient for generating the alarm signal 1341.

Figure 3:
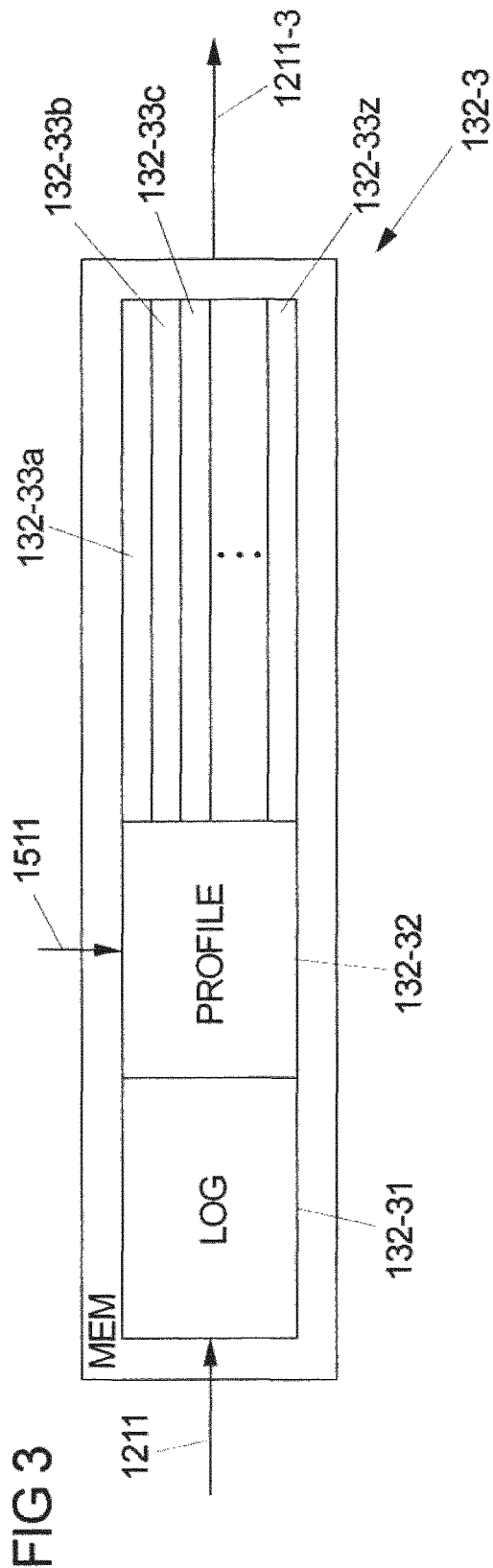
FIG. 3 is a schematic and exemplary view of an embodiment of a storage device of the second signal evaluation mechanism of the mobile monitoring device according to the principles of the present invention.

The reliability of the mobile monitoring device 1 can be increased by the use of the storage device 132-3 of which an embodiment is schematically shown in FIG. 3. The storage device 132-3 comprises a data logger (LOG) 132-31 that receives the body measurement signal 1211. The data logger 132-31 continuously records data being indicative of the measured body property signal 1211 received during an elapsed time period with a predetermined duration. The time period can be, for example, a few hours, a few days or also only a few minutes or seconds. For example, the data logger 132-31 records the history of the speed and of the direction of motion of the person, which facilitates the recognizing of abnormal motion states such as a "dragging locomotion" or a "staggering."

The data logger 132-31 is coupled to a profile generation unit (PROFILE) 132-32 that generates measured body property profiles dependent on the data recorded by the data logger 132-31. The respective profiles are filed by the profile generation unit 132-32 in storage areas 132-33a ... 132-33z. The number of storage areas can be freely selected. In addition, the profile generation unit 132-32 receives a user recognition 1511 that was inputted via the input device 15 of the mobile monitoring device 1. Therefore, different measured body property profiles can be stored for different users of the mobile monitoring device 1. Individual storage areas are freed according to which user is using the mobile monitoring device 1, which areas are then the basis for the comparison which the comparator 132-4 carries out between the feature signal 1211-2 and the measured body profiles.

As a result of the fact that use is made of the measured body property profiles, anomalies in the detected measured body property can be more readily detected and therefore the alarm signal 1341 can be more reliably produced.

The measured body property profiles can be, as was already explained in the general part, for example, motion profiles, for example, motion patterns (so-called motion patterns). In particular, certain motion patterns such as a "dragging locomotion", "staggering", "fall", etc., that can be reliably recognized based on the data logger.

All the previously cited components of the mobile monitoring device 1 are shown only schematically and by way of illustration in FIG. 1 to FIG. 4. The individual components do not have to be arranged structurally separated from each other as is suggested in the figures but rather the respective functionality can also be implemented in a common processor. An important feature of the present invention is the simultaneous consideration of the body signal 1321 and of the gas signal 1311 so that the decision about whether an alarm signal is generated or not is not made on the basis of an isolated consideration of both signals but rather in particular also on the basis of a correlation of these signals. Another feature of the present invention is the use of measured body property profiles. This allows the more reliable detection of anomalies in the body measurement signal.

LIST OF REFERENCE NUMERALS

1 mobile monitoring device
11 gas measurement device
111 gas measurement interface
1111 gas measurement signal
12 body measurement device
121 body measurement interface
1211 body measurement signal
1211-1 weighted body measurement signal
1211-2 feature signal
1211-3 body measuring signal profile
13 control unit
131 first signal evaluation means
131-1 analysis unit
1311 gas signal
1312 control signal
132 second signal evaluation means
132-1 weighting unit
132-2 feature extractor
132-3 storage device
132-31 data logger
132-32 profile generation unit
132-33a, . . . , 132-33z storage areas
132-4 comparator
1321 body signal
133 correlator
133-1 comparison unit
1331 correlation signal
134 controller
1341 alarm signal
14 transmitter
15 input means
1511 user recognition
1512 gas signal threshold value
1513 body signal threshold value

What is claimed is:

1. A method for operating a mobile monitoring device, comprising:
reading a value of a measured gas property of a gas, the gas being in the environment around the mobile monitoring device, and providing a gas measurement signal dependent on the read value of the measured gas property;
reading a value of a measured physical body property of a body of a person wearing the mobile monitoring device and providing a body measurement signal dependent on the read value of the measured body property;
receiving the gas measurement signal and the body measurement signal by a control unit for controlling the mobile monitoring device;
determining a correlation signal dependent on a degree of correlation between a gas signal derived from the gas measurement signal and a body signal derived from the body measurement signal; and
controlling the mobile monitoring device to (1) generate an alarm signal when the correlation signal indicates that the gas signal or body signal exceeds or drops below a first predetermined threshold value and (2) enter an energy-saving mode when the correlation signal drops below a second predetermined threshold value and the gas signal is below a predetermined threshold value.

2. A mobile monitoring device, comprising:
a first measuring device configured to detect a gas and generate a gas signal based on the detected gas;
a second measuring device configured to detect a physical trait associated with a user of the mobile monitoring device and generate a body signal based on the detected physical trait;
a correlator configured to generate a correlation signal based on the gas signal and the body signal; and
a control unit configured to control the mobile monitoring device to (1) generate an alarm signal when the correlation signal indicates that the gas signal or body signal exceeds or drops below a first predetermined threshold value and (2) enter an energy-saving mode when the correlation signal drops below a second predetermined threshold value and the gas signal is below a predetermined threshold value.

3. The mobile monitoring device of claim 2, wherein the control unit is configured to control the mobile monitoring device in response to the correlation signal to perform a task comprising at least one of the following: generating an alarm, operating in a normal mode, entering a sleep mode, or any combination thereof.

4. The mobile monitoring device of claim 2, wherein the gas signal represents detection of a gas characteristic comprising at least one of the following: toxicity of the gas, explosiveness of the gas, pressure of the gas, temperature of the gas, oxygen content of the gas, or any combination thereof.

5. The mobile monitoring device of claim 2, wherein the body signal represents detection of a characteristic of a physiological trait comprising at least one of the following: body acceleration, body speed, relative body position, heart functionality, respiratory functionality, temperature, blood pressure, or any combination thereof.

6. The mobile monitoring device of claim 2, further comprising a transmitter configured to transmit an alarm signal to a central monitoring device.

7. A method, comprising:
detecting, using a gas measurement device of a mobile monitoring device, a gas that surrounds the mobile monitoring device;
generating, using the gas measurement device, at least one gas signal based on the detecting of the gas;
detecting, using a body measurement device of the mobile monitoring device, a physical trait associated with a user of the mobile monitoring device;

generating, using the body measurement device, at least one body signal based on the detecting of the physical trait;
generating, using a correlator of the mobile monitoring device, a correlation signal utilizing the body signal and the gas signal; and
controlling, using the control unit of the mobile monitoring device, the mobile monitoring device to (1) generate an alarm signal when the correlation signal indicates that the gas signal or body signal exceeds or drops below a first predetermined threshold value and (2) enter an energy-saving mode when the correlation signal drops below a second predetermined threshold value and the gas signal is below a predetermined threshold value.

* * * * *